US011696944B2

(12) United States Patent
Jacobs

(10) Patent No.: US 11,696,944 B2
(45) Date of Patent: *Jul. 11, 2023

(54) **VACCINE FOR PROTECTION AGAINST *STREPTOCOCCUS SUIS***

(71) Applicant: Intervet Inc., Madison, NJ (US)

(72) Inventor: Antonius Arnoldus Christiaan Jacobs, Kessel (NL)

(73) Assignee: Intervet Inc., Madison, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 17/290,828

(22) PCT Filed: Nov. 7, 2019

(86) PCT No.: PCT/EP2019/080482
§ 371 (c)(1),
(2) Date: May 3, 2021

(87) PCT Pub. No.: WO2020/094762
PCT Pub. Date: May 14, 2020

(65) Prior Publication Data
US 2021/0369832 A1  Dec. 2, 2021

(30) Foreign Application Priority Data
Nov. 8, 2018  (EP) .................................... 18205251

(51) Int. Cl.
*A61K 39/09* (2006.01)
*A61P 31/04* (2006.01)
*A61K 39/00* (2006.01)

(52) U.S. Cl.
CPC ............ *A61K 39/092* (2013.01); *A61P 31/04* (2018.01); *A61K 2039/552* (2013.01)

(58) Field of Classification Search
None
See application file for complete search history.

(56) References Cited

FOREIGN PATENT DOCUMENTS

WO      2015181356 A1    12/2015
WO      WO-2017005913 A1 *  1/2017  ........... A61K 39/092

OTHER PUBLICATIONS

Database Protein [Online], Jan. 30, 2014 (Jan. 30, 2014), "Mac family protein [*Streptococcus suis* JS14]", XP002796691, retrieved from NCBI, Database accession No. ADV69609, 2 pages.
Extended European Search Report for U.S. Appl. No. 18/205,251 4 dated Jan. 22, 2019.
Goyette-Desjardins, , G, et al, Protection against *Streptococcus suis* Sero type 2 Infection Using a Capsular Polysaccharide Glycoconjugate Vaccine, Infection and Immunity, 2016, pp. 2059-2075, vol. 84,No. 7.
Hu, et al, Complete Genome Sequence of *Streptococcus suis* Serotype 14 Strain JS14, Journal of Bacteriology, May 2011, pp. 2375-2376, vol. 193, No. 9.
Protein-XP002787007 Retrieved from NCBI, database accession No. AUW23484.
Seele, J et al, The immunoglobulin M-degrading enzyme of *Streptococcus suis*, Idessuiss, is involved in complement evasion, Veterinary research, 2015, pp. 45, vol. 46.
Seele, J et al, The immunoglobulin M-degrading enzyme of *Streptococcus suis*, IdeSsuis, is a highly protective antigen against serotype 2, Vaccine, 2015, pp. 2207-2212, vol. 33 No. 19, Elsevier, EP.

* cited by examiner

*Primary Examiner* — Oluwatosin A Ogunbiyi
(74) *Attorney, Agent, or Firm* — David J. Kerwick

(57) ABSTRACT

The present invention pertains to a vaccine comprising an IgM protease antigen of *Streptococcus suis*, for use in a method for protecting pigs against an infection with *Streptococcus suis* of serotype 2 and against an infection with *Streptococcus suis* of serotype 14.

5 Claims, No Drawings

VACCINE FOR PROTECTION AGAINST STREPTOCOCCUS SUIS

CROSS-REFERENCE TO RELATED APPLICATIONS

This application is a National Stage application of International Patent Application No. PCT/EP2019/080482, filed Nov. 7, 2019, which claims priority to European Patent Application No. EP 18205251.4, filed Nov. 8, 2018.

GENERAL FIELD OF THE INVENTION

The invention pertains to the protection of pigs against a pathogenic infection with *Streptococcus suis* bacteria of various serotypes.

BACKGROUND OF THE INVENTION

*Streptococcus suis* (*S. suis*) is one of the principal etiologic agents of contagious bacterial disease in pigs. The pathogen can cause a variety of clinical syndromes including meningitis, arthritis, pericarditis, polyserositis, septicaemia, pneumonia and sudden death. *S. suis* is a gram-positive facultatively anaerobic coccus, originally defined as Lancefield groups R, S, R/S or T. Later, a new typing system based on the type-specific capsular polysaccharide antigens located in the cell wall was proposed. This led to a system comprising 35 serotypes (Rasmussen and Andresen, 1998, "16S rDNA sequence variations of some *Streptococcus suis* serotypes", Int. J. Syst. Bacteriol. 48, 1063-1065) of which serotypes 2, 9, 1, 7 and 1/2 are the most prevalent, whereas serotype 14 is emerging in particular across Europe. Control of *Streptococcus suis* in pig herd appears to be very difficult. *Streptococcus suis* is a commensal and opportunistic pathogen of swine. Apparently, the immune system is not triggered in each and every occasion of an infection. Next to this, *Streptococcus suis* is a well-encapsulated pathogen and uses an arsenal of virulence factors to evade the host immune system. Together, these characteristics have challenged the development of efficacious vaccines to fight this important pathogen. Recently, an overview article has been published regarding vaccines against *Streptococcus suis* (Mariela Segura: "*Streptococcus suis* vaccines: candidate antigens and progress, in Expert Review of Vaccines, Volume 14, 2015, Issue 12, pages 1587-1608). In this review, clinical field information and experimental data have been compiled and compared to give an overview of the current status of vaccine development against *Streptococcus suis* as outlined here below.

Currently used vaccines are mainly whole-cell bacterins. However, field reports describe difficulty in disease control and management, and specially "vaccine failures" are common. Carrier pigs are the primary source of infection, and both vertical and horizontal transmission are involved in spread of the disease within a herd. Mixing of carrier animals with susceptible animals under stressful conditions such as weaning and transportation usually results in clinical disease. Early medicated weaning and segregated early weaning practices do not eliminate *Streptococcus suis* infection. Therefore, effective control measures to prevent disease will hinge on prophylactic/metaphylactic procedures (where allowed) and on vaccination. Currently, field immunization efforts have focused on the use of commercial or autogenous bacterins. These vaccine strategies have been applied to either piglets or sows. From weaning and onwards piglets are more susceptible to *Streptococcus suis* infections due to the stresses associated with weaning and also, the common subsequent transport. Therefore, prepartum immunization in sows is often used to try and convey passive immunity to piglets and provide protection against *Streptococcus suis* under these stressful circumstances early in life. Moreover, sow vaccination is less costly and labor intensive, thus representing an economical alternative to piglet vaccination. Yet, available results seem to indicate that sow vaccination with bacterins is also a matter of controversy. In many cases vaccinated sows, even when vaccinated twice before parturition, respond poorly or not at all to vaccination which results in low maternal immunity transferred to the litters. And even if maternal immunity is transferred at a sufficient level, in many cases the maternal antibodies are too low to provide protection in the most critical period of 4-7 weeks of age.

In piglets, autogenous bacterins are frequently used in the field, especially in Europe. They are prepared from the virulent strain isolated on the farm with clinical problems and applied to the same farm. One of the disadvantages of autogenous bacterins is that vaccine safety data are lacking and severe adverse reactions may occur. Sampling errors (due to using only one or two pigs or samples) may result in failure to identify a strain or serotype associated with a recent outbreak. This failure may be especially problematic in endemic herds. Finally, the most important dilemma of autogenous bacterins is that their actual efficacy has been poorly studied. As application of autogenous vaccines is empirical, it is not surprising that results obtained with these vaccines are inconsistent.

Other experimental vaccines are also described in the art. Kai-Jen Hsueh et al. show ("Immunization with *Streptococcus suis* bacterin plus recombinant Sao protein in sows conveys passive immunity to their piglets", in: *BMC Veterinary Research, BMC series—open, inclusive and trusted*, 13:15, 7 Jan. 2017) that a bacterin plus subunit might be a basis for successful vaccination of sows to confer protective immunity to their piglets.

Live attenuated vaccines have also been contemplated in the art. Non encapsulated isogenic mutants of *Streptococcus suis* serotype 2 have been clearly shown to be avirulent. Yet, a live vaccine formulation based on a non encapsulated serotype 2 mutant induced only partial protection against mortality and failed to prevent the development of clinical signs in pigs challenged with the wildtype strain (Wisselink H J, Stockhofe-Zurwieden N, Hilgers L A, et al. "Assessment of protective efficacy of live and killed vaccines based on a non-encapsulated mutant of *Streptococcus suis* serotype 2." in: *Vet Microbiol.* 2002, 84:155-168.)

In the last couple of years, an extensive list of antigenic or immunogenic *Streptococcus suis* molecules has been reported, and most of these have been discovered through immuno proteomics using either convalescent sera from infected pigs or humans and/or laboratory-produced immune sera. WO2015/181356 (IDT Biologika GmbH) has shown that IgM protease antigens (either the whole protein or the highly conserved Mac-1 domain representing only about 35% of the full protein) can elicit a protective immune response in piglets in a vaccination scheme of administering two doses of the IgM protease antigen, optionally in combination with a prime vaccination containing a bacterin. It is noted that WO2017/005913 (Intervacc AB) also describes the use of an IgM protease antigen (in particular, an IgM protease polypeptide fused to a nucleotidase). However, only the property of being able to elicit a seroresponse has been shown. A protective effect for an IgM protease antigen is not shown in this international patent application.

Another factor that increases the problem of providing adequate protection against *Streptococcus suis* is the lack of heterologous protection of existing vaccines. For example, Porcilis Strepsuis® is a registered vaccine (available from MSD Animal Health and Coopers Animal Health) to protect swine against *Streptococcus suis* serotype 2. It also passively protects the offspring against serotype 2 via intake of the colostrum. Also, as known from WO 2010/108977, when the vaccine is administered to sows, the offspring seems to have some (very low) level of protection against heterologous challenge. However, such passive protection is only very short lived. Next to this, the vaccine was never registered for protection of offspring via the intake of colostrum against *Streptococcus suis* bacteria of any other serotype, so apparently the level of heterologous protection was too low to meet registration standards. This is in line with the common knowledge that for *Streptococcus suis* vaccines, protection against bacteria of serotypes not comprised in the vaccine does not occur. This is confirmed i.a. in the PhD thesis of Hendrikus Jan Wisselink, titled "*Streptococcus suis* infection in pigs: Use of virulence-associated markers in diagnostics and vaccines", published 6 Dec. 2001. In the summary (page 129) it is stated that a "strategy to prevent disease caused by *S. suis* is by the use of vaccines. Killed whole-cell vaccines seem to induce significant protection against challenge with a strain of homologues serotype, but this protection is probably serotype-specific".

These findings are in line with the findings by Smith (U.S. Pat. No. 7,125,548; published 24 Oct. 2006). She states that "antibodies are serotype-specific, and will often only confer protection against only one of the many serotypes known within a group of Streptococci. For example, current commercially available *S. suis* vaccines, which are generally based on whole-cell-bacterial preparations, or on capsule-enriched fractions of *S. suis*, confer only limited protection against heterologous strains" (column 4, lines 42-28 of the US patent). A study published in January 2008 (Medycyna Weterynaryjna, Volume 64, issue 1, pages 113-116), describes protection against *S. suis* bacteria of serotypes 2 and 1/2. If there would be any expected level of heterologous protection between different serotypes, it would be between these serotypes since they are immunologically very closely related. Still, both serotypes were comprised in the vaccine to obtain adequate protection. The UK based RUMA (Responsible Use of Medicines in agriculture Alliance) has published guidelines on the use of vaccines and vaccination in pig production in November 2006. With respect to disease caused by *S. suis*, these guidelines state (on page 19) that protection of the pig can be achieved by vaccination of the sow, but that "protection against disease caused by other *Strep. suis* serotypes is unlikely to occur."

OBJECT OF THE INVENTION

It is an object of the invention to find a vaccine that is effective in protection of pigs against *Streptococcus*, in particular against bacteria of two prevalent serotypes 2 and 14. It is a further object to arrive at a level of protection against bacteria of both serotypes that corresponds (at least) with the level of protection of existing commercially available bacterin vaccines.

SUMMARY OF THE INVENTION

In order to meet the main object of the invention it has been found that an IgM protease antigen of *Streptococcus suis* can be used in a method for protecting pigs against a pathogenic infection with *Streptococcus suis* of serotype 2 and against a pathogenic infection with *Streptococcus suis* of serotype 14. The IgM protease antigen is typically comprised in a vaccine composition, i.e. a composition safe to be administered to the pigs, in which composition the antigen is mixed with a pharmaceutically acceptable carrier for ease of administration. By administering the antigen to the pigs, it was found that the pigs are protected against a pathogenic infection with *Streptococcus suis* bacteria of serotype 2 and serotype 14. It was even found that the level of protection against both serotypes corresponds to the level of homologous protection arrived at when using a conventional serotype 2 bacterin vaccine (cf Porcilis Strepsuis). This means that heterologous protection has been shown for the IgM protease antigen, at least between serotypes 2 and serotype 14. This is the first time that adequate active protection against *Streptococcus suis* bacteria of at least serotypes 2 and serotype 14 has been shown by using only one antigen, in particular the first time that this has been shown using an IgM protease antigen. This provides the unique option to vaccinate the pigs themselves and induce active heterologous protection, instead of relying on the short lived passive protection that can be obtained via the colostrum of immunised mother animals as known from WO2010/108977. Next to this, the actual level of protection, both homologous and heterologous, appears to be significantly better than obtainable with the known bacterin type vaccine.

The invention also pertains to the use of an IgM protease antigen of *Streptococcus suis* for the manufacture of a vaccine for protecting pigs against a pathogenic infection with *Streptococcus suis* of serotype 2 and against a pathogenic infection with *Streptococcus suis* of serotype 14, and to a method for protecting pigs against a pathogenic infection with *Streptococcus suis* of serotype 2 and against a pathogenic infection with *Streptococcus suis* of serotype 14, by administering a vaccine comprising an IgM protease antigen of *Streptococcus suis* to the pigs.

As noted here above, in a vaccine the antigen is typically combined with a pharmaceutically acceptable carrier, i.e. a biocompatible medium, viz. a medium that after administration does not induce significant adverse reactions in the subject animal, capable of presenting the antigen to the immune system of the host animal after administration of the vaccine. Such a pharmaceutically acceptable carrier may for example be a liquid containing water and/or any other biocompatible solvent or a solid carrier such as commonly used to obtain freeze-dried vaccines (based on sugars and/or proteins), optionally comprising immunostimulating agents (adjuvants). Optionally other substances such as stabilisers, viscosity modifiers or other components are added depending on the intended use or required properties of the vaccine.

Definitions

An IgM protease antigen of *Streptococcus suis* is an enzyme that specifically degrades porcine IgM (and not porcine IgG or porcine IgA; Seele at al, in *Journal of Bacteriology*, 2013, 195 930-940; and in Vaccine 33:2207-2212; 5 May 2015), a protein denoted as IdeSsuis, or an immunogenic part thereof (typically having a length of at least about 30-35% of the full length enzyme). The whole enzyme has a weight of about 100-125 kDa, corresponding to about 1000-1150 amino acids, the size depending on the serotype of *S. suis*. In WO 2015/181356 several sequences that represent an IgM protease antigen of *Streptococcus suis* are given, viz. SEQ ID NO:1, SEQ ID NO:2, SEQ ID NO:6, SEQ ID NO:7 and SEQ ID NO:5, the latter being an immunogenic part of the full length enzyme (denoted as the Mac-1 domain, i.e. amino acids 80-414 of SEQ ID NO:7). Other examples of immunogenic parts of the full length enzyme are given in WO2017/005913. In particular the IgM protease may be the protease according to SEQ ID NO:1 of WO2015/1818356 or a protein having at least 90%, or even 91, 92, 93, 94, 95, 96, 97, 98, 99% up to 100% sequence identity in the overlapping regions. The amino acid sequence identity may be established with the BLAST program using the blastp algorithm with default parameters. It is expected that the IgM protease of *Streptococcus suis* of various serotypes have a sequence identity higher than 90%, in particular expected to be 91, 92, 93, 94, 95, 96, 97, 98, 99% up to 100%. An artificial protein, for example made to optimize yield in a recombinant production system of the antigen, may lead to a lower amino acid sequence identity such as 85%, 80%, 75%, 70% or even 60% compared with the whole enzyme, while maintaining the required immunogenic function, and is understood to be an IgM protease antigen of *Streptococcus suis* in the sense of the present invention.

Protection against a pathogenic infection with a micro-organism is the same as arriving at protective immunity, i.e. aiding in preventing, ameliorating or curing the pathogenic infection with that micro-organism or a disorder arising from that infection, for example to prevent or reduce of the actual infection or one or more clinical signs resulting from the pathogenic infection with the pathogen.

A method comprising administering an antigen only once means that protective immunity is conferred after only one single shot of the antigen, and thus, that a booster vaccination is omitted to arrive at the said protective immunity. In a two-shot regime, the first (prime) vaccination is typically boosted within 6 weeks from the first administration, commonly within 3 or even 2 weeks from the first administration, and only after the second (boost) administration protective immunity, i.e. a successful protection as defined here above, is understood to be obtained.

EMBODIMENTS OF THE INVENTION

In a first embodiment of the present invention the method comprises administering the antigen only once to the pigs. Unexpectedly, only one shot of the antigen appears to be capable of eliciting protective immunity in the pigs. In the art, non-live *Streptococcus suis* vaccines have always been administered in a prime-boost regime, and still, led to relatively poor efficacy. Regarding the antigen for use in the current invention, the art (see WO2015/181356 and WO2017/005913) has consistently used this antigen in a two-shot administration approach, optionally using a multi-way vaccine (i.e. more than only the IgM protease antigen). It was therefore highly surprising to find that a single dose with the IgM protease is able to induce protective immunity in pigs.

In a second embodiment the method comprises administering the antigen to the pigs at an age of at most 28 days. As indicated here above, *Streptococcus suis* is a commensal and opportunistic pathogen of swine. In particular under stress, the bacterium may elicit a pathogenic infection and induce disease. Under modern pig producing conditions, major stress is induced on or after the pigs reach an age of 28 days, for example induced by the weaning of piglets (3-4 weeks) and transport of young piglets soon thereafter. In order to be protected against a pathogenic infection with *Streptococcus suis*, the pigs thus need to receive their vaccine at a very young age, typically before they reach the age of 28 days. It was found that by using an IgM protease antigen in pigs at an age of at most 28 days, i.e. any age of 1, 2, 3, 4, 5, 6, 7, 8, 9, 10, 11, 12, 13, 14, 15, 16, 17, 18, 19, 20, 21, 22, 23, 24, 25, 26, 27 or 28 days, adequate (heterologous) protection may be obtained. As is known form the art, in particular from WO2017/005913, a positive immune response against an IgM protease antigen can be obtained in young pigs from the day of birth and onwards. This means that by the present showing of actual protection in 25 day old pigs, it is understood that protection can be obtained even at a younger age.

In another embodiment the method comprises administering the antigen before an age at which the pigs are weaned. In other words, the antigen is administered before the piglets are actually weaned (typically at an age of 3-4 weeks). It has been shown that using the antigen at this early age, heterologous protection can be obtained against a pathogenic infection with *Streptococcus suis*, induced by stress within a short window of 2-3 weeks right after weaning. It is acknowledged that WO2015/181356 shows successful vaccination using an IgM protease as antigen. However, apart from the fact that heterologous protection was not shown, the vaccine was used in piglets having an age of 5-7 weeks and receiving a challenge infection at an age of 9 weeks, thus well after the risk period (i.e. the period of peak incidence of pathogenic *Streptococcus suis* infections) of 2-3 weeks after weaning/transport, i.e. 5-7 weeks of age. So without any proof of effectiveness under practical circumstances (i.e. challenge infection in the window 2-3 weeks after weaning and transportation stress) it is still questionable, apart from the question whether heterologous protection would be arrived at, whether the IgM protease/bacterin combination vaccine strategy as described in WO 2015/181356 under practical circumstances.

In again another embodiment the method comprises administering the antigen to pigs having maternally derived anti-*Streptococcus suis* antibodies. Active vaccination of young animals has the concern of possible interference with maternal antibodies, either produced by natural infection or by active immunization of sows (Baums C G, Bruggemann C, Kock C, et al. "Immunogenicity of an autogenous *Streptococcus suis* bacterin in preparturient sows and their piglets in relation to protection after weaning", in: *Clin Vaccine Immunol.* 2010; 17:1589-1597). Indeed, neither vaccination of suckling nor of weaning piglets from immunized sows was associated with a prominent active immune response and protection at 8 weeks of age. This failure was associated with a strong inhibitory effect of maternal antibodies or other colostrum components. In this regard, interference between maternal antibodies and active production of antibodies against *S. suis* could also be demonstrated in a field study after vaccination with an autogenous *S. suis* capsular type 1/2 vaccine formulation (Lapointe L, D'Allaire S, Lebrun A, et al.: "Antibody response to an autogenous vaccine and serologic profile for *Streptococcus suis* capsular type 1/2." in: *Can J Vet Res.* 2002; 66:8-14. A field study aimed at determining the efficacy of a single-dose *S. suis* serotype 14 bacterin protocol in 4-day-old suckling piglets also failed to protect piglets against homologous challenge (Amass S F, Stevenson G W, Knox K E, et al. "Efficacy of an autogenous vaccine for preventing streptococcosis in piglets" in: *Vet Med.* 1999, 94, 480-484). It came therefore as a surprise that with the IgM protease antigen, adequate protection could even be obtained in the presence of maternally derived ant-*Streptococcus suis* antigens.

In yet another embodiment the method is for conferring protection against mortality associated with a pathogenic infection with *Streptococcus suis* of serotype 2 and serotype 14.

In still another embodiment the method is for conferring protection against clinical signs associated with a pathogenic infection with *Streptococcus suis* of serotype 2 and serotype 14. Typical clinical signs associated with a pathogenic infection with *Streptococcus suis* are increased rectal temperature, impaired locomotion (limping, swollen joints), increased respiration rate and neurological signs (e.g. tremors, convulsions, torticollis, ataxia). Preventing, amelioration or curing one or more of these signs will be beneficial for the pig, apart from being an indication that the pathogenic infection is being suppressed.

The invention will now be further explained based on the following examples.

EXAMPLES

Example 1

The aim of the first study was to test whether an IgM protease antigen, in this case IgM protease antigen of *Streptococcus suis* serotype 2, is able to provide protection against a challenge with *Streptococcus suis* of serotype 2 in comparison to a regular bacterin vaccine containing killed serotype 2 *S. suis* bacteria (cf. Porcilis Strepsuis).

Study Design

Thirty weaned pigs were used. The pigs were allotted to three groups (evenly distributed over the different litters) of 10 pigs each. Group 1 was vaccinated twice intramuscularly at 5 and 7 weeks of age with a recombinant rIdeSsuis IgM protease antigen (Seele et al: Vaccine 33:2207-2212; 5 May 2015, par. 2.2.) at 230 µg per dose (as established by a Bradford protein assay using BSA as a standard) in oil-in-water adjuvant. Group 2 was vaccinated twice intramuscularly at 5 and 7 weeks of age with a serotype 2 whole cell bacterin (cf Porcilis Strepsuis) in oil-in-water adjuvant (positive control). Group 3 was left unvaccinated and served as challenge control. At 9 weeks of age the pigs were challenged with a virulent culture of *S. suis* serotype 2. At regular times before and after challenge heparin blood was collected for re-isolation of challenge strain. After challenge the pigs were observed daily for clinical signs of *S. suis* infection (such as depression, locomotory problems and/or neurological signs) and scored using a regular scoring system going from 0 (no signs) to 3 for severe cases. Severely affected animals were euthanized and post-mortem examined. At the end of the study (7 days after challenge) all surviving pigs were euthanized and post-mortem examined.

Results

None of the vaccines induced any unacceptable site or systemic reactions and thus could be considered safe. The post challenge data for the period before euthanisation (at day 7) are indicated in Table 1. It is noted that on the day of challenge one pig in Group 1 appeared to be a runt and it was decided not to challenge this animal. The average clinical scores, the number of dead animals after challenge and the number of animals from which the pathogen could be re-isolated from the blood appeared to be improved for both vaccines.

TABLE 1

| | Post challenge data Study 1 | | |
| Group | Average clinical score | Dead after challenge | Positive blood isolation |
| --- | --- | --- | --- |
| 1 | 11 | 1/9 | 2/9 |
| 2 | 33 | 5/10 | 6/10 |
| 3 | 61 | 10/10 | 10/10 |

Conclusion

As expected, the inactivated whole cell vaccine induced significant homologous protection. The IgM protease antigen induced even better protection against an infection with *Streptococcus suis* serotype 2.

Example 2

The aim of the second study was to test whether the IgM protease antigen is able to provide protection against a challenge with *Streptococcus suis* of serotype 14.

Study Design

The design of the study was in essence the same as of the first study. Groups of 10 pigs were used and vaccinated twice at the age of 5 and 7 weeks with the IgM protease antigen (Group 1) or they were left as unvaccinated control animals (Group 2). At 9 weeks of age the pigs were challenged with a virulent culture of *S. suis* serotype 14.

Results

Also in this study the vaccine did not induce any unacceptable site or systemic reactions. On day of first vaccination (5 weeks of age) most pigs had a (maternally derived) antibody titre of about 4 log 2. After vaccination, the vaccine group showed good antibody responses with average antibody titres of 9.3 log 2 after booster vaccination. The antibody titres of the control animals remained at a low level with average antibody titres of 4.1 log 2. The post challenge data for the period before euthanisation (at day 11 after challenge) are indicated in Table 2 (ACS=average clinical score; APT=average peak temparture; AST=average survival time; DAC=Dead after challenge; PBI=positive blood isolation)

TABLE 2

| | Post challenge data Study 2 | | | | |
| Group | ACS | APT | AST | DAC | PBI |
| --- | --- | --- | --- | --- | --- |
| 1 | 1.3 | 40.0 | 11.0 | 0/10 | 0/10 |
| 2 | 16.9 | 40.5 | 9.4 | 2/10 | 2/10 |

Conclusion

Although in this study the challenge appeared to be less virulent, the results demonstrate that the IgM protease antigen induces protection against *S. suis* serotype 14 challenge. This was demonstrated by a reduction in clinical scores, the number of animals reaching the humane endpoint, and the number of animals from which the challenge bacterium could be reisolated from the blood. Next to this it appeared that the average survival time for the vaccinated animals was better. Together with the data of the first study, the conclusion can be drawn that the IgM protease antigen is able to provide protection against a pathogenic *Strepto-*

*coccus suis* infection with bacteria of serotype 2 and serotype 14. This means, also taking into account the high identity between IgM protease of serotype 2 and IgM protease of serotype 14, that cross-protection between these serotypes has been demonstrated (i.e. IgM protease of *Streptococcus suis* serotype 2 protects against serotype 14 challenge and vice versa). Also, it appears that the level of protection against both serotypes corresponds to (or is even better) than the level of homologous protection obtainable with a commonly available serotype 2 bacterin vaccine.

Example 3

As protection against *Streptococcus suis* for pigs is preferably obtained in the risk period (typically 4-7 weeks of age) it was assessed whether an IgM protease containing vaccine is efficacious as a one shot vaccine in maternally derived anti-*Streptococcus suis* positive pigs at an age of 3 weeks.

Study Design

The study design was comparable to that of the first two studies, with the main difference that instead of 5 week old animals, 3 week old anti-Ssuis MDA positive piglets were vaccinated (only 1 out of 10 animals appeared to have an MDA level below detection limit). Group 1 was vaccinated once intramuscularly with the IgM protease antigen in an oil-in-water adjuvant. Group 2 served as a negative challenge control group. At 4 weeks of age the piglets were weaned. At 6 weeks of age the piglets were transported to the challenge room and challenged immediately. There was no acclimatization period between the transport and the challenge to mimic natural stress. The piglets were challenged with a virulent culture of *Streptococcus suis* serotype 2.

Results

The vaccines did not induce any unacceptable site or systemic reactions. The post challenge data for the period before euthanisation (at day 7) are indicated in Table 3. On the day of challenge one pig in Group 2 appeared to be a runt and it was decided not to challenge this animal.

TABLE 3

Post challenge data Study 3

| Group | Average clinical score | Dead after challenge | Positive blood isolation |
|---|---|---|---|
| 1 | 18 | 3/10 | 3/10 |
| 2 | 43 | 7/9 | 7/9 |

Conclusion

In conclusion, the results demonstrate that by administering the IgM protease antigen only once adequate protection can be induced in 3 week old MDA positive piglets against a pathogenic infection with *Streptococcus suis*, even when challenged 3 weeks after vaccination, 2 weeks after weaning and immediately after transport. Although this has been demonstrated with a serotype 2 challenge only, since example 2 shows that the antigen is capable of inducing protection against serotype 14 as well, it is understood that comparable results are obtained when aiming at protection against a serotype 14 infection in this type of pigs.

The invention claimed is:

1. A method for protecting a pig against both a pathogenic infection with *Streptococcus suis* of serotype 2 and a pathogenic infection with *Streptococcus suis* of serotype 14, comprising administering a vaccine comprising an IgM protease antigen of *Streptococcus suis* to the pig; wherein the pig has maternally derived anti-*Streptococcus suis* antibodies.

2. The method for protecting the pig of claim 1, comprising administering the antigen only once to the pig.

3. The method for protecting the pig of claim 1, comprising administering the antigen to the pig at an age of at most 28 days.

4. The method for protecting the pig of claim 1, comprising administering the antigen before an age at which the pig is weaned.

5. The method for protecting the pig of claim 1, wherein the method confers protection against mortality associated with a pathogenic infection with *Streptococcus suis* of serotype 2 and serotype 14.

* * * * *